United States Patent [19]

Duranleau

[11] 4,092,327

[45] May 30, 1978

[54] PREPARATION OF ISOXAZOLINES

[75] Inventor: Roger G. Duranleau, Bridge City, Tex.

[73] Assignee: Texaco Inc., New York, N.Y.

[21] Appl. No.: 738,996

[22] Filed: Nov. 5, 1976

[51] Int. Cl.$^2$ .......................................... C07D 261/20
[52] U.S. Cl. .......................... 260/307 DA; 260/307 F; 252/392
[58] Field of Search .................... 260/307 F, 307 DA

[56] References Cited

PUBLICATIONS

Wiley, "The Chemistry of Heterocyclic Compounds" vol. 7, (1962), Interscience Publishers, pp. 96–97.

*Primary Examiner*—Raymond V. Rush
*Attorney, Agent, or Firm*—Thomas H. Whaley; Carl G. Ries; George J. Darsa

[57] ABSTRACT

3-Acylisoxazolines are prepared by reacting an alkene with an alpha-nitroketone in the presence of an organic acid catalyst.

25 Claims, No Drawings

PREPARATION OF ISOXAZOLINES

BACKGROUND OF THE INVENTION

This invention relates to a method of preparing 3-acylisoxazolines. In particular, this invention relates to a novel method of preparing 3-acylisoxazolines by reacting alkenes with alpha-nitroketones.

Isoxazolines, such as acylisoxazolines, can be prepared by the action of an acid, such as hydrochloric acid on an unsaturated alpha-diketone, monooxime or by reacting an alpah-ethylenic ketone, such as 2-butenone, and a nitrile oxide. The aforementioned methods are not particularly attractive inasmuch as the starting materials are difficult to prepare. Moreover, Quilico et al., Nature, vol. 166, page 226 (1956) and Grundmann and Grunanger, The Nitrile Oxides, Springer-Verlag (1971) describe the preparation of 2-isoxazolines by the 1,3-dipolar cycloaddition of nitrile oxides to alkenes. Nitrile oxides are generally unstable materials and a main difficulty, apart from the threat of explosion, resides in the nitrile oxide's rapid spontaneous polymerization or dimerization to furoxanes. One method for preparing nitrile oxides, such as benzonitrile oxide is by dehydrochlorination of the corresponding hydroximyl acid chloride by the action of an inorganic or organic base in either an aqueous or anhydrous organic medium. Tertiary amines have been evaluated as dehydrochlorinating agents for hydroximic acid chlorides dissolved or supsended in ether, but may react with hydroximic acid chlorides to form stable addition compounds instead of nitrile oxides. The use of two separate reaction stages for rearing isoxazolines is disadvantageous, particularly where the first stage dehydrohalogenation is conducted at a substantially lower temperature than the second stage cycloaddition. Such a procedure involving a plurality of stages conducted at different temperatures results in economic penalties and detracts from the commercial attractiveness of the overall process.

It is therefore an object of this invention to provide a novel method for preparing 3-acylisoxazolines.

Another object of this invention is to provide a method for preparing 3-acylisoxazolines from alphanitroketones and alkenes by a one step reaction.

Yet another object of this invention is to provide a method for preparing 3-acylisoxazolines from materials having long storage lives.

Other objects and advantages will become apparent from the following detailed description and examples.

SUMMARY OF THE INVENTION

Broadly, this invention contemplates a method of preparing 3-acylisoxazolines which comprises contacting an alkene and an alpha-nitroketone in the presence of catalytic amounts of an organic acid having a $pk_a$ of about 4.0 to about 0.5.

Pursuant to this invention, the contemplated isoxazolines are prepared from a $C_5$ to $C_{20}$ alkene, suitably a $C_6$ to $C_{16}$ alkene including olefins and cycloalkenes corresponding to the formula $R^1$— CH = CH —$R^2$. In the formula, $R^1$ and $R^2$ can be hydrogen, or an alkyl group having from 1 to 18 carbon atoms or an alkylene group having from 1 to 18 carbon atoms or an aryl group having from 6 to 18 carbon atoms or where $R^1$ and $R^2$ together form a polymethylene group of 1 to 18 carbons. A combination of groups may be present, as for example $R^1$ may be hydrogen and $R^2$ alkyl, or $R^1$ may be alkyl and $R^2$ aryl. Illustrative of the alkenes, I mentioned 1-pentene, 2-pentene, cyclopentene, 3methylcyclopentene, 3-hexene, cyclohexene, 2-heptene, cycloheptene, 4-methylcyclohexane, 4-phenylcyclohexene, 1-octene, 1,7-octadiene, cyclooctene, styrene, beta-methylstyrene, 1-decene, cyclodecene, cyclododecene, 1-dodecene, diphenylethylene, 1-tetradecene, 4-tetradecene, dibenzylethylene, 7-heptadecene, cyclooctadecene, cycloeicosene and 10-eicosene. Mixtures of alkenes, such as 1-pentene and 2-pentene; 3-methylcyclohexene, 4-methylcyclohexene and cycloheptene; 4-dodecene and 5-dodecene; or mixtures of $C_6$ to $C_{14}$ or $C_{10}$ to $C_{14}$ or $C_{14}$ to $C_{18}$ alkenes are similarly contemplated. The instant method is conducted under the conditions described below, such that the alkene is present in the liquid phase.

The second component contemplated in the instant method is an alpha-nitroketone corresponding to the formula:

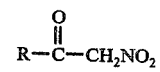

where R is an alkyl group having from 1 to 20 carbon atoms or an aryl group having from 6 to 20 carbon atoms. Illustrative of the alpha-nitroketones contemplated herein can be mentioned 1-nitro-2-propanone, 1-nitro-2-butanone, 1-nitro-2-pentanone, 1-nitro-2-hexanone, 1-nitro-2-heptanone, 1-nitro-2-octanone, 1-nitro-2-decanone, 1-nitro-2-dodecanone, 1-nitro-2-pentadecanone, 1-nitro-2-hexadecanone, 1-nitro-2-heptadecanone, 1-nitro-2-eicosanone, 1-nitro-2-heneicosanone, omega-nitroacetophenone, 4'-tertbutyl-2-nitroacetophenone, 2'-methyl-2-nitroacetophenone, and omega-nitroacetonaphthene.

More specifically, the method of this invention comprises reacting an alkene with an alpha-nitroketone as hereinabove described at a temperature of from about 50° to 150° C., preferably from about 80° to 110° C. in the presence of a catalyst. The catalysts contemplated in the present method are organic acids having a $pk_a$ of about 4.0 to about 0.5, preferably about 2.0 to 0.5. In general, the organic acids have 2 to 18 carbons. For purposes of illustration I mention as catalysts organic sulfonic acids of 6 to 18 carbons such as p-toluenesulfonic acid, m-toluenesulfonic acid, p-bromobenzenesulfonic acid, p-chlorobenzenesulfonic acid, 2,6-naphthalenedisulfonic acid, 1-naphthalenesulfonic acid, 2-naphthalenesulfonic acid, benzenesulfonic acid, 2-mesitylenesulfonic acid and 2-dodecylphenylsulfonic acid; aromatic acids of 7 to 11 carbons such as p-nitrobenzoic acid, m-nitrobenzoic acid, 2-methyl-4-nitrobenzoic acid, 2-butyl-4-nitrobenzoic acid and p-nitrophenylacetic acid; and alpha-halogenated alkanoic acids of 2 to 5 carbons such as chloroacetic acid, dichloroacetic acid, trichloroacetic acid, dichloropropanoic acid and dichlorobutanoic acid. The preferred catalysts are the organic sulfonic acids, particularly p-toluenesulfonic acid. The use of inorganic acids such as sulfuric acid or hydrochloric acid are excluded from the present method in that they are poorly miscible in the reaction mixture. Further, the introduction of water by use of such aqueous inorganic acids is deleterious to the present method leading to competing reactions such as the formation of acids or amides.

The catalytic reaction is typically conducted in the presence of non-reactive, non-polar organic solvent illustrated by benzene, toluene, xylene, chlorobenzene, carbontetrachloride, hexane, heptane, cyclohexane, cycloheptane, 2,2,4-trimethylpentane, decane, dodecane, decaline, tetraline and the like. Suitably the solvent has the boiling point of between about 70° to 250° C. Highly preferred solvents are benzene and toluene. The use of a polar solvent, such as alcohols or low molecular weight carboxylic acids, is deleterious to the method in that polar solvents are reactive with the nitroketone and lead to the formation of, for example, esters or amides. Moreover, the use of excessive amounts of alkene can be employed as a partial or total replacement for the non-reactive, non-polar organic solvent. The reaction should also be conducted in an essentially non-aqueous environment, that is, in the substantial absence of added water. The reaction described herein is sensitive to water and water introduced in amounts exceeding about 0.1 weight percent based on the weight of the nitroketone promote competing reactions and the formation of acids and amides instead of the desired products. Moreover, water is a by-product of the instant catalytic reaction and it is preferred to separate the water produced during the reaction as soon as practicable. For example, a batch catalytic reaction is conducted, the water formed can be continuously removed from the reaction zone by, for example, conducting the method under partial refluxing conditions and at atmospheric pressure with continuous slow distillation of the reaction solvent. In continuous operations as when the nitroketone and catalyst are continuously contacted and passed through a reaction zone, the water produced can be separated by distillation. Any unconverted nitroketone and alkene may be recycled and again contacted with the catalyst along with fresh materials.

Pursuant to the method, the alkene, alpha-nitroketone and catalyst are contacted in a mole ratio of nitroketone to alkene of between above about 1:1 and 1:200, preferably between about 1:25 and 1:100. In general reaction times are from one-quarter to 24 hours employing the reaction temperatures described above leading to the good production of desired product. At the completion of the reaction the isoxazoline product can be recovered by initially contacting the reaction mixture with an aqueous alkaline solution, such as aqueous sodium bicarbonate, at below the reaction temperature, typically at about room temperature, thereby neutralizing the acid catalyst. After separating the aqueous layer containing the neutralized catalyst, the isoxazoline can be recovered from the organic layer containing the product, any unconverted nitroketone, alkene and solvent (if employed) by, for example, distillation. The purity of the recovered product can be further improved by recrystallization.

The 3-substituted isoxazolines prepared according to this invention correspond to the formula:

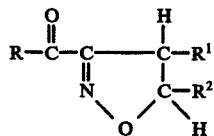

where R, $R^1$ and $R^2$ are as defined above. When the alkene of choice is a 1-alkene, such as 1-octene, the instant method produces a 3-acyl-5-alkylisoxazoline such that $R^1$ is hydrogen and $R^2$ is a hexyl group. In those instances where an internal alkene is used, such as 2-pentene, 3-acyl-4,5-dialkylisoxazolines are produced, where $R^1$ and $R^2$ are respectively methyl and ethyl or ethyl and methyl. The use of a cycloalkene, such as cyclohexene forms 3-acyl-4,5-cycloalkylisoxazolines. Illustrative of the isoxazolines provided by the method can be mentioned 3-acetyl-5-propylisoxazoline, 3-propanoyl-5-butylisoxazoline, 3-butanoyl-5-hexylisoxazoline, 3-pentanoyl-5-octylisoxazoline, 3-hexanoyl-5-decyisoxazoline, 3-hexanoyl-4-methyl-5-ethylisoxazoline, 3-octanoyl-5-methylisoxazone, 3-decanoyl-5-octadecylisoxazoline, 3-dodecanoyl-4,5-diethylisoxazoline, 3-dodecanoyl-4,5-[2-phenyl]cyclotetramethyleneisoxazoline, 3-dodecanoyl-4,5-[phenyl]cyclotetramethyleneisoxazoline, 3-tridecanoyl-5-octylisoxazoline, 3-tetradecanoyl-4-phenyl-5-methylisoxazoline, 3-pentadecanoyl-5-tetradecylisoxazoline, 3-hexadecanoyl-5-hexylisoxazoline, 3-hexadecanoyl-4,5-cyclotetramethyleneisoxazoline, 3-hexanoyl-4,5-cyclohexamethyleneisoxazoline, 3-hexadecanoyl-5-[6-hexylene]isoxazoline, 3-hexadecanoyl-5-dodecylisoxazoline, 3-hexadecanoyl-4,5-dibenzylisoxazoline, 3-benzoyl-5-octylisoxazoline, 3-benzoyl-4,5-diphenylisoxazoline, 3-benzoyl-5-dodecylisoxazoline and 3-[-2-methylbenzoyl]-5-heptanoylisoxazoline. The isoxazolines prepared by the method of this invention are useful as corrosion inhibitors and as additives to fuels and lubricants. Corrosion inhibiting compositions wherein the isoxazolines can be utilized are described in, for example, U.S. Pat. No. 2,564,423. The compounds are also useful as intermediates in the preparation of other valuable products as amine derivatives and other derivatives are useful as photographic sensitizers and dyes for color photography.

In order to more fully illustrate the nature of this invention and in the manner of practicing the same, the following examples are presented.

EXAMPLE 1

A reaction mixture composed of 12.33 grams (0.05 mole) of 1-nitro-2-tetradecanone, 50 milliliters of toluene, 175 milliliters of 1-octene and 1.5 grams (0.0079 mole) of p-toluenesulfonic acid were heated to reflux for seven and one-half hours. Thereafter, the reaction mixture was cooled to room temperature and filtered. The filtrate was washed with a five percent aqueous sodium bicarbonate solution and water. The organic layer was recovered, dried and evaporated to dryness and 13.36 grams of a tan solid recovered. The solid was recrystallized from carbon tetrachloride and was identified by infrared analyses as 3-tridecanoyl-5-hexylisoxazoline.

EXAMPLE 2

Following the procedure of Example 1, 3-benzoyl-5-phenylisoxazoline is prepared employing 8.2 grams (0.05 mole) of omega-nitroacetophenone, 50 milliliters of toluene, 175 milliliters of styrene and 1.5 grams of benzenesulfonic acid.

EXAMPLE 3

In the manner described in Example 1, 3-acetyl-4,5-diphenylisoxazoline is prepared employing 5.15 grams (0.05 mole) of 1-nitro-2-propanone, 150 milliliters of toluene, 100 grams of 1,2-diphenylethylene and 1.5 grams of trichloroacetic acid.

EXAMPLE 4

As described in Example 1, 3-pentadecanoyl-4,5-tetramethyleneisoxazoline is prepared utilizing 14.3 grams (0.05 mole) of 1-nitro-2-hexadecanone, 50 milliliters of toluene, 175 milliliters of cyclohexene and 1.5 grams of p-toluenesulfonic acid.

EXAMPLE 5

Following the procedure of Example 1, 3-nonanoyl-4-methyl-5-ethylisoxazoline is prepared employing 10.0 grams (0.05 mole) of 1-nitro-2-decanone, 50 milliliters of toluene, 175 milliliters of 2-pentene and 1.5 grams of p-toluenesulfonic acid.

I claim:

1. A method of preparing 3-acylisoxazolines which comprises contacting a $C_5$ to $C_{20}$ alkene corresponding to the formula $R^1$—CH=CH—$R^2$, wherein $R^1$ and $R^2$ can be hydrogen, alkyl having from 1 to 18 carbon atoms, aryl having from 6 to 18 carbon atoms, or wherein $R^1$ and $R^2$ taken together form a polymethylene group of 1 to 18 carbon atoms, and an alpha-nitroketone of the formula

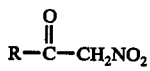

where R is an alkyl group of 1 to 20 carbon atoms or an aryl group of 6 to 20 carbon atoms in the presence of catalytic amounts of an organic acid having 2 to 18 carbon atoms and a $pk_a$ of about 4.0 to about 0.5 at a temperature of from about 50° to 150° C.

2. A method of preparing 3-acylisoxazolines which comprises contacting a $C_5$ to $C_{20}$ alkene corresponding to the formula $R^1$—CH=CH—$R^2$ where $R^1$ and $R^2$ are hydrogen or an alkyl group having from 1 to 18 carbon atoms and an alpha-nitroketone of the formula:

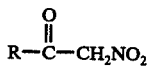

where R is an alkyl group of 1 to 20 carbon atoms in the presence of catalytic amounts of an organic acid having 2 to 18 carbon atoms and a $pk_a$ of about 4.0 to about 0.5 at a temperature of from about 50° to 150° C. and where the mole ratio of nitroketone to alkene is between about 1:25 and 1:100.

3. A method according to claim 1 wherein said contacting is at a temperature of from about 80° to 110° C.

4. A method according to claim 1 wherein said alkene has from 6 to 16 carbon atoms.

5. A method according to claim 1 wherein said alkene is 1-octene.

6. A method according to claim 1 wherein said alkene is styrene.

7. A method according to claim 1 wherein said alkene is 1,2-diphenylethylene.

8. A method according to claim 1 wherein said alkene is cyclohexene.

9. A method according to claim 1 wherein said alkene is 2-pentene.

10. A method according to claim 1 wherein said nitroketone is 1-nitro-2-tetradecanone.

11. A method according to claim 1 wherein said nitroketone is omega-nitroacetophenone.

12. A method according to claim 1 wherein said nitroketone is 1-nitro-2-propanone.

13. A method according to claim 1 wherein said nitroketone is 1-nitro-2-hexadecanone.

14. A method according to claim 1 wherein said nitroketone is 1-nitro-2-decanone.

15. A method according to claim 1 wherein said organic acid is an alpha-halogenated alkanoic acid of 2 to 5 carbons.

16. A method according to claim 1 wherein said acid is an aromatic nitro acid of 7 to 11 carbon atoms.

17. A method according to claim 1 wherein said acid is an organic sulfonic acid of 6 to 18 carbon atoms.

18. A method according to claim 1 wherein said acid is p-toluenesulfonic acid.

19. A method according to claim 1 wherein said acid is benzenesulfonic acid.

20. A method according to claim 1 wherein said acid is trichloroacetic acid.

21. A method according to claim 1 wherein said contacting is conducted in the presence of a non-reactive, non-polar solvent.

22. A method according to claim 15 wherein said solvent is toluene.

23. A method according to claim 1 wherein by-product water is continuously separated from the reaction.

24. A method according to claim 1 wherein said isoxazoline is 3-tetradecanoyl-5-hexylisoxazoline.

25. A method of preparing 3-tridecanoyl-5-hexylisoxazoline which comprises contacting 1-octene and 1-nitro-2-tetradecanone in the presence of catalytic amounts of an organic acid having 2 to 18 carbon atoms and $pk_a$ of about 4.0 to about 0.5 at a temperature of from about 50° to 150° C. and where the mole ratio of said nitroketone to 1-octene is between about 1:25 and 1:100.

* * * * *